United States Patent
Hanafusa et al.

(10) Patent No.: US 8,293,521 B2
(45) Date of Patent: Oct. 23, 2012

(54) METHOD OF DISPENSING NONVOLATILE LIQUID IN REACTION VESSEL AND REACTION VESSEL PROCESSING APPARATUS

(75) Inventors: Nobuhiro Hanafusa, Kyoto (JP); Koretsugu Ogata, Kyoto (JP); Ryuh Konoshita, Kyoto (JP); Yusuke Nakamura, Kanagawa (JP); Yozo Ohnishi, Kanagawa (JP)

(73) Assignees: Shimadzu Corporation, Kyoto (JP); Toppan Printing Co., Ltd., Tokyo (JP); Riken, Saitama (JP)

( * ) Notice: Subject to any disclaimer, the term of this patent is extended or adjusted under 35 U.S.C. 154(b) by 871 days.

(21) Appl. No.: 11/887,357

(22) PCT Filed: Mar. 30, 2006

(86) PCT No.: PCT/JP2006/306733
§ 371 (c)(1),
(2), (4) Date: Nov. 7, 2008

(87) PCT Pub. No.: WO2006/106868
PCT Pub. Date: Oct. 12, 2006

(65) Prior Publication Data
US 2010/0221704 A1    Sep. 2, 2010

(30) Foreign Application Priority Data
Mar. 30, 2005   (JP) ................. 2005-100256

(51) Int. Cl.
*C12M 1/36*   (2006.01)
*C12M 1/38*   (2006.01)
*C12M 3/00*   (2006.01)

(52) U.S. Cl. ............... 435/286.4; 435/288.7; 435/286.1; 435/287.2; 435/288.3; 435/288.5

(58) Field of Classification Search ............... 435/286.4, 435/6.1, 286.1, 287.1, 287.2, 287.3, 288.3, 435/288.5, 288.7
See application file for complete search history.

(56) References Cited

U.S. PATENT DOCUMENTS

| | | | |
|---|---|---|---|
| 6,335,166 B1 * | 1/2002 | Ammann et al. | 435/6.11 |
| 2001/0041357 A1 * | 11/2001 | Fouillet et al. | 435/91.1 |
| 2002/0127660 A1 * | 9/2002 | Danssaert et al. | 435/91.3 |
| 2003/0180191 A1 * | 9/2003 | Suzuki et al. | 422/102 |

FOREIGN PATENT DOCUMENTS

JP    04-346800    12/1992

(Continued)

OTHER PUBLICATIONS

International Search Report (PCT/ISA/210) for App. No. PCT/JP2006/306733 mailed May 16, 2006 (4 pages total with English translation).

*Primary Examiner* — Michael Marcheschi
*Assistant Examiner* — Shanta G Doe
(74) *Attorney, Agent, or Firm* — Cheng Law Group, PLLC

(57) ABSTRACT

It is intended to easily dispense a minute amount of nonvolatile liquid. In a preferred embodiment, in dispensing of mineral oil (nonvolatile liquid), dispensing is conducted in the condition that the amount of air contained in a tip (70) is small by aspirating a larger amount of mineral oil (40) than a single dispensing amount in the tip (70) of a nozzle (28).

2 Claims, 13 Drawing Sheets

FOREIGN PATENT DOCUMENTS

| | | |
|---|---|---|
| JP | 05-252993 | 10/1993 |
| JP | 06-273426 | 9/1994 |
| JP | 09-238687 | 9/1997 |
| JP | 09-322755 | 12/1997 |
| JP | 2001-299366 | 10/2001 |
| JP | 2002-048805 | 2/2002 |
| JP | 2002-162401 | 6/2002 |
| JP | 2002-300894 | 10/2002 |
| JP | 2002-533096 | 10/2002 |
| JP | 2004-532003 | 10/2004 |
| WO | WO 00/37679 | 6/2000 |
| WO | WO 02/060584 | 8/2002 |

\* cited by examiner

Invader reaction and fluorescence detection, allele judgment

METHOD OF DISPENSING NONVOLATILE LIQUID IN REACTION VESSEL AND REACTION VESSEL PROCESSING APPARATUS

TECHNICAL FIELD

The present invention relates to a reaction vessel processing apparatus for detecting a genome DNA polymorphism for plants and animals including human beings, particularly an SNP (single-nucleotide polymorphism) using a reaction vessel which is suited for various automatic analyses in medical fields, for example, research of gene analysis or clinic, as well as for chemical reactions. Using the detected gene polymorphism detection result, diagnosis of disease morbidity, diagnosis of the relationship between the type and effect or side effect of a drug administered and the like may be achieved.

BACKGROUND ART

A method and apparatus for estimating susceptibility to diseases, etc., by using gene polymorphism have been proposed as follows:

For determining whether a patient is susceptible to sepsis and/or rapidly develops sepsis, a nucleic acid sample is collected from the patient, a pattern 2 allelic gene or a marker gene which is in linkage disequilibrium with a pattern 2 allelic gene in the sample is detected, and if a pattern 2 allelic gene or a marker gene in linkage disequilibrium with a pattern 2 allelic gene is detected, the patient is judged to be susceptible to sepsis (see Patent Literature 1).

For diagnosis of one or more single-nucleotide polymorphisms in the human flt-1 gene, a sequence of one or more positions in human nucleic acid, that is, positions 1953, 3453, 3888 (which are respectively in accordance with numbering in EMBL Accession No. X51602), 519, 786, 1422, 1429 (which are respectively in accordance with numbering in EMBL Accession No. D64016), 454 (in accordance with Sequence No. 3) and 696 (in accordance with Sequence No.: 5) is determined, and by referring to the polymorphism in fl1-1 gene, the constitution of the human is determined (JP-A 2001-299366).

Many methods have been reported on typing, that is, discrimination of bases in SNP sites. A typical example of these methods is as follows:

For carrying out typing several hundred thousand SNP sites with a relatively small amount of genome DNA, a plurality of base sequences containing at least one single-nucleotide polymorphism are amplified simultaneously with a genome DNA and pairs of primer, and a plurality of base sequences thus amplified are used to discriminate bases in single-nucleotide polymorphic sites contained in the base sequences by a typing step. For the typing step, an invader method or TaqMan PCR is used (see Patent Literature 3).

Patent Literature 1: Japanese Patent Application National Publication (Laid-Open) No. 2002-533096
Patent Literature 2: JP-A 2001-299366
Patent Literature 3: JP-A 2002-300894
Patent Literature 4: Japanese Patent No. 3452717

DISCLOSURE OF THE INVENTION

Problems to be Solved by the Invention

The inventors of the present invention have proposed a reaction vessel suited for automating measurement of a chemical reaction and gene polymorphism detection for the purpose of measurements of a chemical reaction and automatic detection of a gene polymorphism. The reaction vessel includes at least a reaction part that allows a reaction of a sample, and a nonvolatile liquid reservoir for reserving a nonvolatile liquid such as mineral oil having a lower specific gravity than a reaction solution. At the time of use, a nonvolatile liquid is dispensed to the reaction part to cover the surface of a reaction solution.

When a nonvolatile liquid is dispensed to the reaction part by a dispenser, the dispensing amount may sometimes be as small as several microliters. Dispensing of a liquid by a nozzle is usually achieved by aspirating a single dispensing amount into a nozzle and completely discharging the same. However, since the nonvolatile liquid to be dispensed has viscosity, even if a syringe that leads to the nozzle is pushed to discharge such a minute amount, it is impossible to dispense an accurate amount due to viscosity of the nonvolatile liquid and compression of air, and hence the accuracy of dispensing is poor.

There is also a case when dispensing of a nonvolatile liquid fails due to the nonvolatile liquid adhering on the outer face of a tip end of the nozzle.

When a reaction is conducted after dispensing a reaction solution to a reaction part in the condition that the top face of the reaction solution cannot be covered with a nonvolatile liquid and is exposed, there arises a problem that the reaction solution evaporates during a reaction to hinder measurement with high accuracy.

It is an object of the present invention to make it possible to easily dispense a minute amount of a nonvolatile liquid to a reaction part of a reaction vessel for preventing evaporation of a reaction solution.

Means for Solving the Problems

The method of the present invention is a nonvolatile liquid dispensing method for dispensing a nonvolatile liquid to a reaction part by a nozzle in a reaction vessel including at least a reaction part for allowing a reaction of a sample and a nonvolatile liquid reservoir for reserving a nonvolatile liquid having a lower specific gravity than a reaction solution, wherein dispensing is conducted while an amount more than a single dispensing amount of the nonvolatile liquid is aspirated and held in the nozzle.

One example of a reaction vessel is a gene polymorphism diagnosing reaction vessel that further includes a typing reagent reservoir reserving a typing reagent, and includes as a reaction part, a plurality of probe arrangement parts each individually holding a probe generating fluorescence in correspondence with each of a plurality of polymorphic sites. In this case, a nonvolatile liquid is dispensed to the probe arrangement parts.

Another example of a reaction vessel is the above gene polymorphism diagnosing reaction vessel that further includes a gene amplification reagent reservoir for reserving a gene amplification reagent containing a plurality of primers to bind to a plurality of polymorphic sites by sandwiching each site between the primers, and further includes as a reaction part, an amplification reaction part that allows a gene amplification reaction for a mixture solution of the gene amplification reagent and the sample. In such a case, a nonvolatile liquid is dispensed also to the amplification reaction part.

As a nonvolatile liquid having a lower specific gravity than a reaction solution, mineral oil, vegetable oil, animal oil, silicone oil, or diphenylether may be used. Mineral oil is a liquid hydrocarbon mixture obtained by distillation from petrolatum, and is also called liquid paraffin, liquid petrolatum, white oil and the like, and includes light oil of low specific gravity. Examples of animal oil include cod-liver oil, halibut oil, herring oil, orange roughy oil, shark liver oil, and the like. Examples of vegetable oil include canola oil, almond oil, cotton seed oil, corn oil, olive oil, peanut oil, safflower oil, sesame oil, soybean oil, and the like.

The reaction vessel processing apparatus of the present invention has a function of executing dispensing of a non-volatile liquid by a nozzle. That is, there are provided a reaction vessel mounting part for mounting a reaction vessel, the reaction vessel having at least a reaction part for allowing a reaction of a sample and a nonvolatile liquid reservoir reserving a nonvolatile liquid for preventing evaporation of a reaction solution in the reaction part; a dispenser 112 for conducting transfer of a liquid of the reaction vessel by moving a nozzle 28 for aspiration and discharge; a controller 118 that controls at least a dispensing operation of the dispenser 112, as shown in FIG. 1, and the controller 118 controls operation of the dispenser 112 so that dispensing is conducted while an amount of equal to or more than a single dispensing amount of the nonvolatile liquid is aspirated and held in the nozzle at the time of dispensing of the nonvolatile liquid.

For externally operating the controller 118 or for displaying a detection result, a personal computer (PC) 122 may be connected to the controller 118.

Effects of the Invention

In the nonvolatile liquid dispensing method of the present invention, since dispensing is conducted while an amount more than a single dispensing amount of a nonvolatile liquid is aspirated and held in a nozzle 28 at the time of dispensing of the nonvolatile liquid by the nozzle 28 of a dispenser 112, the amount of air in the nozzle 28 is small and the influence of compression of air is small, so that a predetermined amount of the nonvolatile liquid can be dispensed to the reaction part.

BEST MODE FOR CARRYING OUT THE INVENTION

FIG. 2A and FIG. 2B show the first example of the reaction vessel, wherein FIG. 2A is a front view, and FIG. 2B is a plan view.

On the same surface side of a plate-like substrate 10, a reagent reservoir part 14 and a nonvolatile liquid reservoir part 16 are formed as concave portions. As the nonvolatile liquid, mineral oil is used, and hereinafter, the nonvolatile liquid reservoir part is referred to as a mineral oil reservoir part. On the same surface side of the substrate 10, further formed is a reaction part 18. The reagent reservoir part 14 and the mineral oil reservoir part 16 are sealed with a film 20, and for aspirating the reagent and the mineral oil and transferring them to other locations by a nozzle, they are aspirated by a nozzle after removal of the film 20, or the film 20 that is adapted to be penetrable by a nozzle is penetrated by the nozzle and the reagent and the oil are aspirated by the nozzle.

The surface of the substrate 10 is covered from above the film 20 with a detachable sealing material 22 of the size that covers the reagent reservoir part 14, the mineral oil reservoir part 16 and the reaction part 18.

One example of concrete use of the reaction vessel is a gene polymorphism diagnosing reagent kit in which a sample reaction solution having DNA amplified by a PCR is dispensed and SNP is detected by an invader reaction.

The relationship between the polymorphic sites and primers is as follows: For amplifying one polymorphic site, a pair of primers binding to the polymorphic site by sandwiching it between primers is necessary. A plurality of kinds of polymorphic sites occur in a target biological sample, and when polymorphic sites occur in positions separated from one another, twice as many kinds of primers as kinds of polymorphic sites are necessary. However, when two polymorphic sites are close to each other, amplification thereof can be effected by binding the primers to each of the polymorphic sites by sandwiching each site between the primers or by binding the primers to both sides of a sequence of the two polymorphic sites with no primer between the polymorphic sites. Accordingly, the types of necessary primers are not always twice as many as kinds of polymorphic sites. In the present invention, "a plurality of primers to bind to a plurality of polymorphic sites by sandwiching each site between the primers" is intended to refer to types of primers necessary for amplifying a plurality of polymorphic sites not only in the case where a pair of primers bind to one polymorphic site by sandwiching it between the primers but also in the case where a pair of primers bind to two or more polymorphic sites by sandwiching a series of such polymorphic sites between the primers.

The polymorphism includes mutation, deletion, overlap, transfer etc. A typical example is SNP.

Examples of the biological sample include blood, saliva, and genome DNA.

One example of the gene amplification reagent is a PCR reagent.

For typing of SNP, adjustment of genome DNA is required at the stage of entering the amplification step, which takes labor and cost Taking a PCR method for amplifying DNA into account, a direct PCR method which is conducted on a sample such as blood without conducting a pre-treatment is proposed According to this proposal, in a nucleic acid synthesis technique for amplifying an objective gene in a sample containing genes, a gene conjugate in a sample containing genes or a sample containing genes itself is added to a gene amplification reaction solution, and an objective gene in the sample containing genes is amplified at a pH ranging from 8.5 to 9.5 (25° C.) in the reaction solution after addition (see Patent document 4).

In a typing system already constructed, only a small amount of DNA is collected first because a plurality of SNP sites to be typed are amplified by a PCR method; however, it is necessary to carry out a pre-treatment for extracting DNA in advance from a biological sample prior to amplification by the PCR method. This takes labor and cost for the pre-treatment.

Such an automated system has not been constructed heretofore that amplifies a plurality of SNP sites to be typed simultaneously when a direct PCR method and a typing method are combined.

The typing step may be achieved by an invader method or a TaqMan PCR method. In such a case, the typing reagent is an invader reagent or a TaqMan PCR reagent.

FIG. 13 schematically shows a detection method for detecting a gene polymorphism using the reaction vessel of the present invention as a gene polymorphism diagnosing reagent kit. In this description, the case where a PCR method is used in an amplification step, and an invader method is used in a typing step, will be explained.

In the PCR step, a PCR regent 4 is added to a biological sample 2 such as blood, or alternatively, the biological sample 2 is added to the PCR reagent 4.

The PCR reagent 4 is prepared in advance, and contains a plurality of primers for SNP sites to be measured, as well as essential reagents such as a pH buffer solution for adjusting pH, four kinds of deoxyribonucleotides, a thermostable synthase, and salts such as $MgCl_2$ and KCl. Besides the above, substances such as a surfactant and a protein may be added as necessary. The PCR method in the amplification step which may be used in the present invention realizes simultaneous amplification of objective plural SNP sites. The biological sample may or may not be subjected to a nucleic acid extraction procedure. When plural genome DNA containing such SNP sites is amplified by the direct PCR method from a biological sample not subjected to the nucleic acid extraction procedure, a gene amplification reaction regent containing a plurality of primers for such SNP sites is caused to act on the biological sample, and the PCR reaction is carried out in the pH condition between 8.5 and 9.5 at 25° C. when mixed with the sample 2.

The pH buffer solution may be a combination of tris(hydroxymethyl)aminomethane and a mineral acid such as hydrochloric acid, nitric acid or sulfuric acid, as well as various pH buffer solutions. The buffer solution having adjusted pH is preferably used at a concentration between 10 mM and 100 mM in the PCR reagent The primer refers to an oligonucleotide acting as a starting point for DNA synthesis by the PCR. The primer may be synthesized or isolated from biological sources.

The synthase is an enzyme for synthesis of DNA by primer addition, and includes chemically synthesized synthases. Suitable synthase includes, but is not limited to, *E. coli* DNA polymerase I, *E. coli* DNA polymerase Klenow fragment, T4 DNA polymerase, Taq DNA polymerase, *T. litoralis* DNA polymerase, Tth DNA polymerase, Pfu DNA polymerase, Hot Start Taq polymerase, KOD DNA polymerase, EX Taq DNA polymerase, and a reverse transcriptase. The term "thermostable" means the property of a compound which maintains its activity even at high temperatures, preferably between 65° C. and 95° C.

In the PCR step, the PCR is caused to occur in a mixture solution of the biological sample 2 and the PCR reagent 4 according to a predetermined temperature cycle. The PCR temperature cycle includes 3 steps, which are denaturation, primer adhesion (annealing) and primer extension, and this cycle is repeated whereby DNA is amplified. In one example of the steps, the denaturation step is carried out at 94° C. for 1 minute, the primer adhesion step at 55° C. for 1 minute, and the primer extension at 72° C. for 1 minute. The sample may be subjected to a genome extraction procedure; however, the one that is not subjected to the genome extraction procedure is used herein. Even with the biological sample not subjected to the genome extraction procedure, DNA is released from blood cells or cells at high temperature in the PCR temperature cycle, and the reagents necessary for the PCR come into contact with the DNA to make the reaction proceed.

After the PCR reaction is finished, an invader reagent 6 is added. A fluorescence-emitting FRET probe and cleavase (structure-specific DNA degradative enzyme) are contained in the invader reagent 6. The FRET probe is a fluorescent-labeled oligo having a sequence completely irrelevant to the genome DNA, and, irrespective of the type of SNP, its sequence is common.

Next, the reaction solution to which the invader reagent 6 has been added is reacted by addition to a plurality of probe arrangement parts 8. At each site of the probe arrangement parts 8, an invader probe and a reporter probe are individually held correspondingly to each of a plurality of SNP sites, and the reaction solution reacts with the invader probe to emit fluorescence if SNP corresponding to the reporter probe is present The invader method is described in detail in paragraphs [0032] to [0034] in Patent Literature 3.

Two reporter probes have been prepared depending on each base of SNP and can judge whether the SNP is a homozygote or heterozygote.

The invader method used in the typing step is a method of typing SNP site by hybridizing an allele-specific oligo with DNA containing SNP as an object of typing, wherein DNA containing SNP as an object of typing, two kinds of reporter probes specific to the each allele of SNP as an object of typing, one kind of invader probe, and an enzyme having a special endonuclease activity by which a structure of DNA is recognized and cleaved are used (see Patent Literature 3).

Next, specific explanation will be made for the reaction vessel. Referring to FIGS. 2A and 2B, an example as a gene polymorphism diagnosing reagent kit will be specifically explained.

On the same face side of a plate-like substrate 10, a sample applying part 12, a typing reagent reservoir 14 and a mineral oil reservoir 16 are formed as concave portions. On the same face side of the substrate 10, a plurality of probe arrangement parts 18 are formed.

A biological sample reaction solution having DNA amplified by a PCR will be injected to the sample injection part 12; however in the condition before use, the sample injection part 12 is provided in an empty state in which a sample is not injected. The typing reagent reservoir part 14 reserves about 10 µL to 300 µL of a typing reagent that is prepared in correspondence with a plurality of polymorphic sites, and the mineral oil reservoir part 16 reserves 20 µL to 300 µL of mineral oil for preventing evaporation of the reaction solution. The typing reagent reservoir part 14 and mineral oil reservoir part 16 are sealed with the film 20 which is penetrable by a nozzle. Such a film 20 is, for example, an aluminum foil or a laminate film with a resin such as aluminum and a PET (polyethylene terephthalate) film, and is bonded by fusion or adhesion so that it will not be readily detached.

Each probe arrangement part 18 individually has a probe that emits fluorescence in correspondence with each of plural polymorphic sites, and is a concave portion capable of holding the mineral oil when it is dispensed from the mineral oil reservoir part 16. Each concave portion of the probe arrangement part 18 is, for example, in the shape of a circle of 100 µm to 2 mm in diameter, and 50 µm to 1.5 mm in depth.

The surface of the substrate 10 is covered from above the film 20 with the detachable sealing material 22 of the size that covers the sample injection part 12, the typing reagent reservoir part 14, the mineral oil reservoir part 16 and the probe arrangement part 18. This sealing material 22 may also be an aluminum foil or a laminate film of aluminum and a resin; however, the bonding strength is smaller than that of the film 20 and is bonded by an adhesive or the like in such a degree that it can be detached.

In order to measure fluorescence from the bottom face side, the substrate 10 is made of a light-permeable resin with a low-spontaneous-fluorescent property (that is, a property of generating little fluorescence from itself), for example, a material such as polycarbonate. The thickness of the substrate 10 is 1 mm to 2 mm.

A method of using the reaction vessel according to the present example will be described.

As shown in FIGS. 3A and 3B, the sealing material 22 is detached at the time of use. The film 20 that seals the typing reagent reservoir part 14 and the mineral oil reservoir part 16 is not detached and still remains.

To the sample injection part 12, 2 µL to 20 µL of a sample reaction solution 24 having DNA amplified externally by a PCR reaction is injected with a pipette 26 or the like. Then the reaction vessel is mounted on the detecting apparatus.

In the detecting apparatus, as shown in FIGS. 4A and 4B, a typing reagent is aspirated by the nozzle 28 inserted into the typing reagent reservoir part 14 through the film 20, and the typing reagent is transferred to the sample injection part 12 by the nozzle 28. In the sample injection part 12, the sample reaction solution and the typing reagent are mixed by repetition of aspiration and discharge by the nozzle 28.

Thereafter, 0.5 µL to 4 µL of the reaction solution of the sample reaction solution and the typing reagent is dispensed to each probe arrangement part 18 by the nozzle 28. To each probe arrangement part 18, 0.5 µL to 10 µL of mineral oil is dispensed from the mineral oil reservoir part 16 by the nozzle 28. Dispensing of mineral oil to the probe arrangement part 18 may be conducted before dispensing of the reaction solution to the probe arrangement part 18. In each probe arrangement part 18, the mineral oil covers the surface of the reaction solution to prevent the reaction solution from evaporating during typing reaction time which is associated with heat generation at the typing reaction temperature control part of the detecting apparatus.

In each probe arrangement part 18, the reaction solution and the probe react, and if a predetermined SNP is present, fluorescence is emitted from the probe. Fluorescence is detected upon irradiation with exciting light from the back face side of the substrate 10.

FIG. 5A, FIG. 5B and FIG. 5C show a second example of the reaction vessel which is processed in the reaction vessel processing apparatus of the present invention. FIG. 5A is a front view, FIG. 5B is a plan view, and FIG. 5C is a section view along the line X-X in FIG. 5B at a gene amplification reaction part.

In this reaction vessel, a biological sample not subjected to a nucleic acid extraction procedure is injected as a sample, and both amplification of DNA by a PCR reaction and SNP detection by an invader reaction are conducted. It is to be noted, however, a biological sample not subjected to a nucleic acid extraction procedure may be injected.

On the same surface side of a plate-like substrate 10a, the sample injection part 12, the typing reagent reservoir part 14, the mineral oil reservoir part 16, and the plurality of probe arrangement parts 18 similar to those in the example of FIG. 2A and FIG. 2B are formed. In this reaction vessel, on the same surface side of the substrate 10a, a gene amplification reagent reservoir part 30, a PCR-finished solution injection part 31, and an amplification reaction part 32 are also formed.

The gene amplification reagent reservoir part 30 is also formed as a concave portion in the substrate 10a, and holds a gene amplification reagent containing a plurality of primers to bind to a plurality of polymorphic sites by sandwiching each site between the primers. The gene amplification reagent reservoir part 30, the typing reagent reservoir part 14 and the mineral oil reservoir part 16 are sealed with the film 20 which is penetrable by a nozzle. The gene amplification reagent reservoir part 30 reserves 2 µL to 300 µL of a PCR reagent In the same way as the example shown in FIG. 2A and FIG. 2B, the typing reagent reservoir part 14 reserves 10 µL to 300 µL of a typing reagent The PCR-finished solution injection part 31 is provided for mixing the reaction solution having finished a PCR reaction in the gene amplification reaction part 32 and the typing reagent, and is formed as a concave portion in the substrate 10a, and provided in an empty state before use.

The gene amplification reaction part 32 allows the mixture solution of the PCR reagent and the sample to proceed a gene amplification reaction.

FIGS. 6A and 6B show an enlarged section view of a part of the gene amplification reaction part 32. FIGS. 6A and 6B show a section view along the line Y-Y in FIG. 5B. As shown in FIGS. 6A and 6B, liquid dispensing ports 34a, 34b of the amplification reaction part 32 have openings 36a, 36b having the shape corresponding to the shape of a tip end of the nozzle 28, and are made of an elastic material such as PDMS (polydimethylsiloxane) or silicone rubber for allowing close fitting to the tip end of the nozzle 28.

The gene amplification reaction part 32 has a smaller thickness in the bottom face side of the substrate 10a so as to improve the heat conductivity, as shown in FIG. 5C, FIGS. 6A and 6B. The thickness of that part is, for example, 0.2 mm to 0.3 mm.

To the sample injection part 12, a biological sample not subjected to a nucleic acid extraction procedure is injected in the present example; however, it is provided in an empty state where a sample is not injected before use.

In the same way as the reaction vessel shown in FIG. 2A and FIG. 2B, the typing reagent reservoir part 14 reserves a typing reagent that is prepared in correspondence with a plurality of polymorphic sites, and the mineral oil reservoir part 16 reserves mineral oil for preventing vaporization of the reaction solution.

In the same way as the reaction vessel shown in FIG. 2A and FIG. 2B, each probe arrangement part 18 individually holds a probe that emits fluorescence in correspondence with each of the plurality of polymorphic sites, and is formed as a concave portion capable of holding mineral oil when the mineral oil is dispensed from the mineral oil reservoir part 16.

The surface of the substrate 10a is covered from above the film 20 with the sealing material 22 which can be detached and has such a size that covers the sample injection part 12, the PCR-finished solution injection part 31, the typing reagent reservoir part 14, the mineral oil reservoir part 16, the gene amplification reagent reservoir part 30, the gene amplification reaction part 32 and the probe arrangement part 18. The materials and the manner of bonding the film 20 and the sealing material 22 are as described in the reaction vessel of FIG. 2A and FIG. 2B.

In order to also measure fluorescence from the bottom side, the substrate 10a is made of a light-permeable resin with a low-spontaneous-fluorescent property, for example, a material such as polycarbonate. The thickness of the substrate 10 is 1 mm to 2 mm.

The manner of using the reaction vessel according to the present example is shown below.

As shown in FIG. 7A and FIG. 7B, the sealing material 22 is detached at the time of use. The film 20 that seals the typing reagent reservoir part 14, the mineral oil reservoir part 16 and the gene amplification reagent reservoir part 30 is not detached and still remains.

To the sample injection part 12, 0.5 µL to 2 µL of a sample 25 is injected with a pipette 26 or the like. In the reaction vessel of FIG. 2A and FIG. 2B, the injected sample is a sample reaction solution having DNA amplified externally by a PCR reaction; however, the sample injected in the present example is a biological sample, for example, blood, not subjected to a nucleic acid extraction procedure. The sample may be a biological sample subjected to a nucleic acid extraction procedure. After application of the sample, the reaction vessel is mounted on a detecting apparatus.

In the detecting apparatus, as shown in FIG. 8A and FIG. 8B, the nozzle 28 is inserted into the gene amplification reagent reservoir part 30 through the film 20 and the PCR reagent is aspirated, and 2 µL to 20 µL of the PCR reagent is transferred to the sample injection part 12 by the nozzle 28. In the sample injection part 12, the sample reaction solution and the PCR reagent are mixed to form a PCR solution by repetition of aspiration and discharge by the nozzle 28.

Next, as shown in FIG. 6A, the PCR solution is injected to the gene amplification reaction part 32 by the nozzle 28. That is, the nozzle 28 is inserted into one port 34a of the gene amplification reaction part 32 and the PCR solution 38 is injected, and then mineral oil 40 is injected to the ports 34a, 34b by the nozzle 28 so as to prevent the PCR solution 38 from evaporating during reaction in the gene amplification reaction part 32, whereby surfaces of the PCR solution 38 in the ports 34a, 34b are covered with the mineral oil 40.

When dispensing this mineral oil 40, an amount larger than a single dispensing amount of the mineral oil 40 is aspirated and held in the tip of the nozzle according to the present invention, and dispensing is conducted in the condition that the amount of air in the tip is small.

After completion of the PCR reaction, the PCR solution is collected by the nozzle 28, and at this time, mineral oil 40 is injected through one port 34a of the gene amplification reaction part 32 as shown in FIG. 6B so as to facilitate the collection. A reaction-finished PCR solution 38a is pushed to the other port 34b. Then the nozzle 28 is inserted and the PCR solution 38a is aspirated into the nozzle 28. Since the ports 34a, 34b have openings 36a, 36b that are formed in correspondence with the shape of the nozzle 28, and made of an elastic material, the nozzle 28 comes into close contact with the ports 34a, 34b to prevent liquid leakage, and facilitate an operation of application and collection of the PCR solution.

The reaction-finished PCR solution 38a collected from the gene amplification reaction part 32 by the nozzle 28 is transferred and injected to the PCR-finished solution injection part 31.

Next the nozzle 28 is inserted into the typing reagent reservoir part 14 through the film 20 and the typing reagent is aspirated, and the typing reagent is transferred and injected to the PCR-finished solution injection part 31 by the nozzle 28. In the PCR-finished solution injection part 31, the PCR solution and the typing reagent are mixed by repetition of aspiration and discharge by the nozzle 28.

Then, 0.5 µL to 4 µL of the reaction solution of the PCR solution and the typing reagent is dispensed to each probe arrangement part 18 by the nozzle 28. To each probe arrangement part 18, 0.5 µL to 10 µL of mineral oil is dispensed by the nozzle 28 from the mineral oil reservoir part 16. Dispensing of mineral oil to the probe arrangement part 18 may be conducted before dispensing of the reaction solution to the probe arrangement part 18. In each probe arrangement part 18, the mineral oil covers the surface of the reaction solution to prevent the reaction solution from evaporating during the period of typing reaction in the typing reaction part of the detecting apparatus, which is associated with heat generation.

In each probe arrangement part 18, the reaction solution and the probe react, and if a predetermined SNP is present, fluorescence is emitted from the probe. Fluorescence is detected upon irradiation with exciting light from the back-face side of the substrate 10.

In the following, the present invention will be described in detail while showing a composition of each reaction reagent however, the technical scope of the present invention is not limited by these examples.

The PCR reagent is known in the art, and a reaction reagent containing a primer, DNA polymerase and TaqStart (available from CLONTECH Laboratories) as described in Patent document 3, paragraph [0046], for example, may be used. Further, AmpDirect (available from SHIMADZU Corporation) may be contained in the PCR reagent As the primer, for example, SNP IDs 1 to 20, SEQ No. 1 to 40 described in Table 1 in Patent document 3 may be used.

As the typing reagent, an invader reagent is used. As the invader reagent, an invader-assay kit (available from Third Wave Technology) is used. For example, a signal buffer, an FRET probe, a structure specific DNase and an allele specific probe are prepared in concentrations as described in Patent document 3, paragraph [0046].

FIG. 9 shows one example of a simplified reaction vessel processing apparatus that uses the above described reaction vessel of the present invention as a reagent kit and detects SNP of a biological sample. In the apparatus, a pair of upper and lower heat blocks 60 and 62 is disposed to constitute a mounting part for a reagent kit, and five reaction vessels 41 of the present invention into which a sample is injected are arranged in parallel on the lower heat block 60. These heat blocks 60, 62 are able to move in the Y direction represented by the arrow.

As shown in FIG. 10, the test reagent kit mounting part has a guiding part that allows sliding of a reaction vessel 41 onto a lower heat block 60 and positions it at a predetermined position. The lower heat block 60 forms an amplification part (not shown) that controls temperature of a gene amplification reaction part 32 in a predetermined temperature cycle. Also provided is a typing reaction part that controls temperature of the probe arrangement parts 18 to such a temperature that causes a reaction between DNA and a probe by both of the heat blocks 60, 62. The amplification part and the typing reaction part are denoted by reference numerals 120, 110, respectively in FIG. 1. The temperature of the amplification part is set to vary in three steps, for example, 94° C., 55° C. and 72° C. in this order, and the cycle is repeated. The temperature of the typing reaction part is set at, for example, 63° C.

The upper heat block 62 constituting the typing reaction part has openings 150 only at the positions corresponding to probe arrangement parts, and also the part that constitutes the typing reaction part in the lower heat block 60 has openings 152 only at the positions corresponding to probe arrangement parts. On the heat block 62, a typing reaction part cover 154 is disposed, and the cover 154 is also provided with openings 156 at the positions of the openings 150 of the heat block 62.

Below the heat block 60, a fluorescence detector 64 for detecting fluorescence is disposed, and the fluorescence detector 64 emits exciting light to a probe arrangement part via the opening 152 of the heat block 60 from the bottom face side of the reaction vessel 41, and detects fluorescence from the probe arrangement part via the opening 152 of the heat block 60 on the bottom face side of the reaction vessel 41. The fluorescence detector 64 moves in the direction of the arrow X in FIG. 9 and detects fluorescence from the probe arrangement parts 18. Fluorescence detection for each probe is achieved by a Y-directional movement of the probe arrangement parts 18 by the test reagent kit mounting part and an X-directional movement of the fluorescence detector 64.

Returning to FIG. 9, for enabling transfer, aspiration and discharge of a liquid by the nozzle 28, a liquid feeding arm 66 that moves in the X, Y and Z directions is provided as a dispenser, and the liquid feeding arm 66 has a nozzle 28. To the tip end of the nozzle 28, a disposable tip 70 is detachably mounted. The dispenser is denoted by reference numeral 112 in FIG. 1.

The nozzle 28 of the dispenser dispenses a reaction solution to a probe arrangement part via the opening 156 of the cover 154 and the opening 150 of the heat block 62, as shown in FIG. 10.

Returning to FIG. 9, in order to control operations of the heat blocks 60, 62, the fluorescence detector 64 and the liquid feeding arm 66, a controller 118 is disposed near these elements. The controller 118 has a CPU and stores a program for operation. The controller 118 controls temperature control of the typing reaction part 110 and the amplification part 120, which are realized by the heat blocks 60, 62, a detection operation of the fluorescence detector 64, and a dispensing operation of the liquid feeding arm 66 of the dispenser 112.

When the reaction vessel 41 not having a gene amplification reaction part as in the case of the reaction vessel of FIG. 2 is used, the amplification part that controls temperature of the gene amplification reaction part is not needed, and there is no need for the controller 118 to have the function for temperature control of the amplification part.

FIG. 11A and FIG. 11B show dispensing of mineral oil onto a reaction solution 170 in a probe arrangement part 18. These drawings show the way of dispensing mineral oil 40 to each probe arrangement part 18 after dispensing the reaction solution 170 to be reacted with the invader probe to each probe arrangement part 18. Even when the mineral oil 40 is dispensed first and then the reaction solution 170 is dispensed, the mineral oil 40 covers the surface of the reaction solution 170 owing to its specific gravity.

FIG. 11A shows a generally conducted method, wherein a single dispensing amount of the mineral oil 40 is aspirated into and discharged from the tip 70 of the nozzle 28. A large volume of air is present in the tip 70, so that the mineral oil 40 could not be discharged due to compression of an air layer when pushed by the syringe.

FIG. 11B shows a mineral oil dispensing method according to the present invention, wherein dispensing is conducted in the condition that the amount of air contained in the tip 70 is small by aspirating a larger amount of the mineral oil 40 than a single dispensing amount in the tip 70. As a result, it is possible to discharge a predetermined amount of mineral oil.

FIG. 12 shows the details of the fluorescence detector 64. The fluorescence detector 64 includes a laser diode (LD) or light-emitting diode (LED) 92 as an exciting light source for emitting a laser light at 473 nm, and a pair of lenses 94, 96 for applying the laser light after collecting it on the bottom face of the probe arrangement part of the reaction vessel 41. The lens 94 is a lens for collecting the laser light from the laser diode 92 to convert it into a parallel light The lens 96 is an objective lens for applying the parallel light after converging it on the bottom face of the reaction vessel 41. The objective lens 96 also functions as a lens for collecting fluorescence emitted from the reaction vessel 41. Between the pair of lenses 94, 96, a dichroic mirror 98 is provided, and wavelength characteristics of the dichroic mirror 98 is established so that an exciting light passes therethrough, while fluorescent light is reflected. On the optical path of a reflected light (fluorescence) of the dichroic mirror 98, a further dichroic mirror 100 is disposed. Wavelength characteristics of the dichroic mirror 100 are established so that a light at 525 nm is reflected, while a light at 605 nm passes therethrough. On the optical path of a light reflected by the dichroic mirror 100, a lens 102, and an optical detector 104 are arranged so as to detect fluorescent light of 525 nm, and on the optical path of a light transmitted the dichroic mirror 100, a lens 106 and an optical detector 108 are arranged so as to detect fluorescent light at 605 nm. By detecting two kinds of fluorescence with the two detectors 104, 108, the presence or absence of SNP corresponding to the invader probe fixed in each probe array position, and whether the SNP is a homozygote or a heterozygote are detected. As a labeled fluorescent substance, for example, FAM, ROX, VIC, TAMRA, Redmond Red and the like may be used.

The detector 64 of FIG. 12 is designed to measure fluorescence of two wavelengths upon irradiation with an exciting light from a single light source; however, the detector 64 may also be designed to use two light sources for enabling irradiation with different exciting wavelengths for fluorescence measurement at two wavelengths.

Industrial Applicability

The present invention may be utilized in various types of automatic analyses, for example, in research of gene analysis or clinical field, as well as in measurement of various chemical reactions. For example, the present invention can be used in detecting genome DNA polymorphism for plants and animals including humans, particularly SNP and can further be utilized, not only in diagnosing disease morbidity, the relationship between the type and effect or side effect of a drug administered and so on by using the results of the above detection, but also in judgment of the variety of animal, or plant, diagnosis of injections (judgment of the type of invader) etc.

Figure 1:
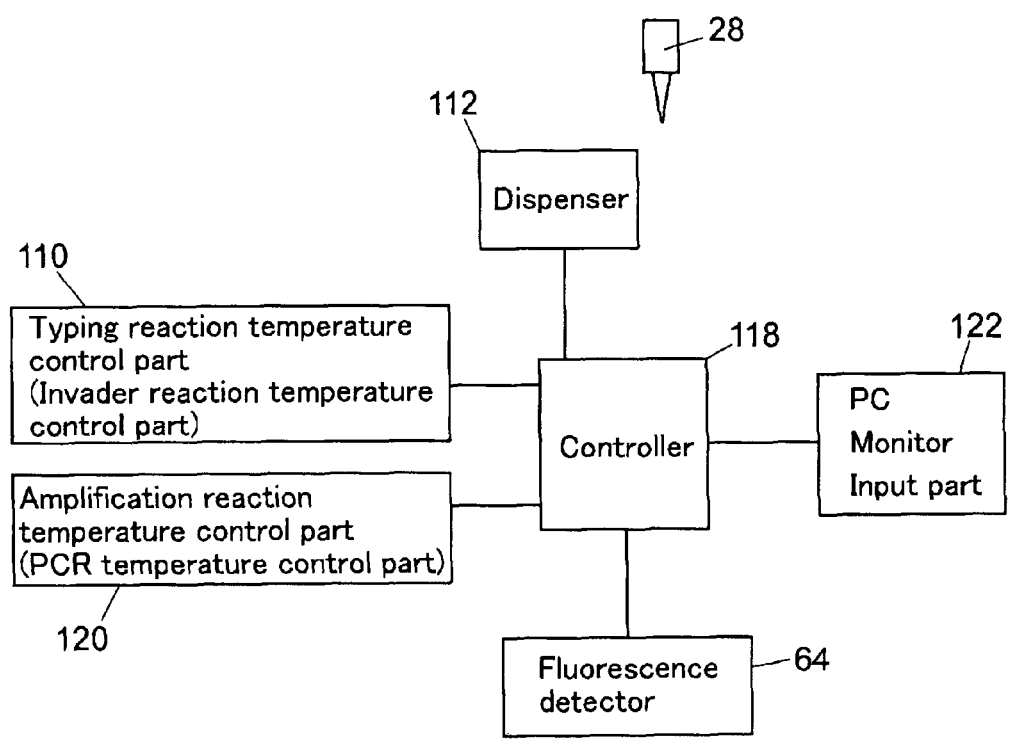
[FIG. 1] A block diagram schematically showing the present invention.
Figure 2A:
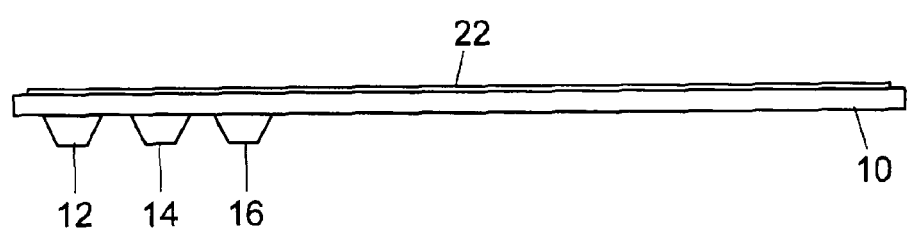
[FIG. 2A] A front view of the first example of a reaction vessel.
Figure 2B:
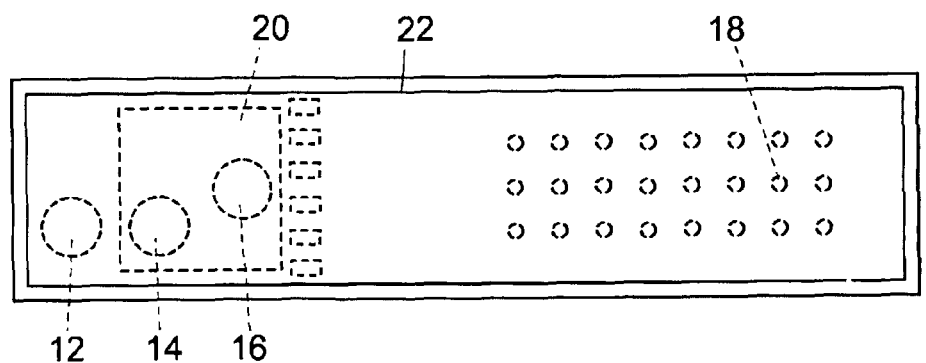
[FIG. 2B] A plan view of the first example of the reaction vessel.
Figure 3A:
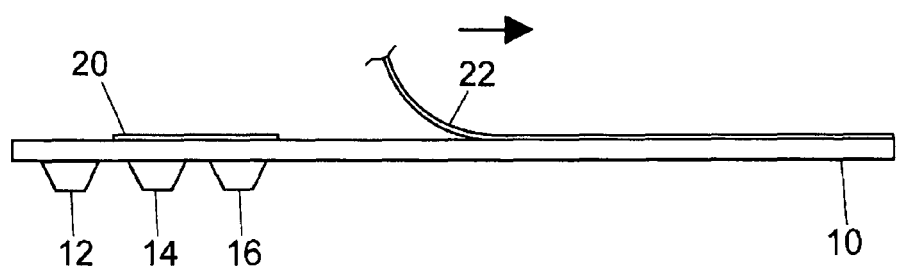
[FIG. 3A] A front view showing a former half of a process of an SNP detection method using the reaction vessel of the same example.
Figure 3B:
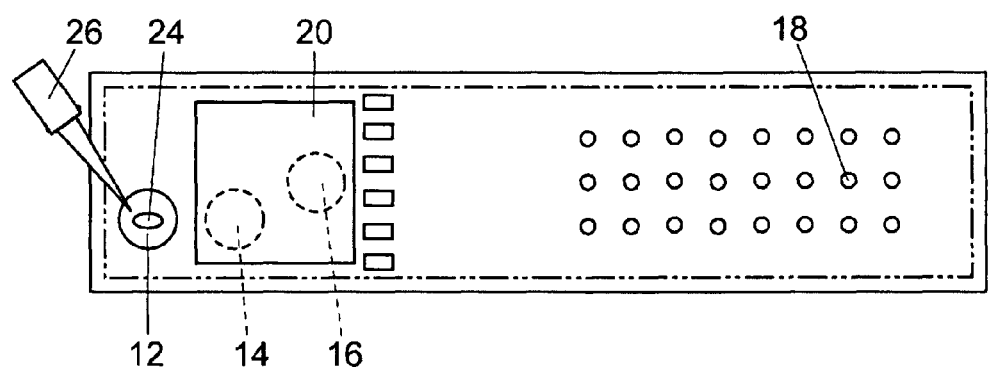
[FIG. 3B] A plan view showing the former half of the process of the SNP detection method using the reaction vessel of the same example.
Figure 4A:
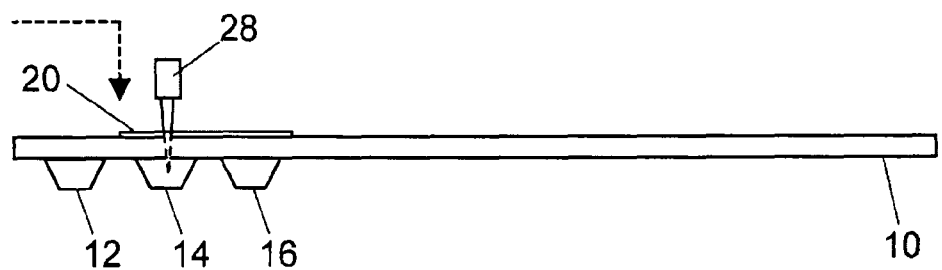
[FIG. 4A] A front view showing a latter half of the process of the SNP detection method using the reaction vessel of the same example.
Figure 4B:
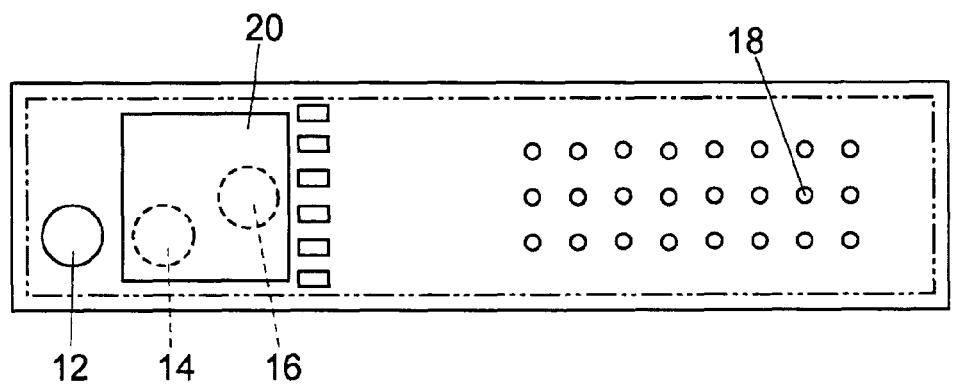
[FIG. 4B] A plan view showing the latter half of the process of the SNP detection method using the reaction vessel of the same example.
Figure 5A:
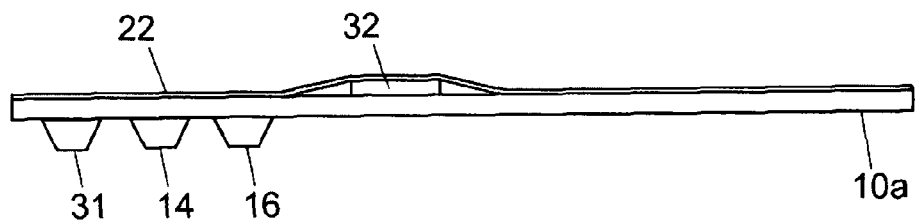
[FIG. 5A] A front view showing the second example of the reaction vessel.
Figure 5B:
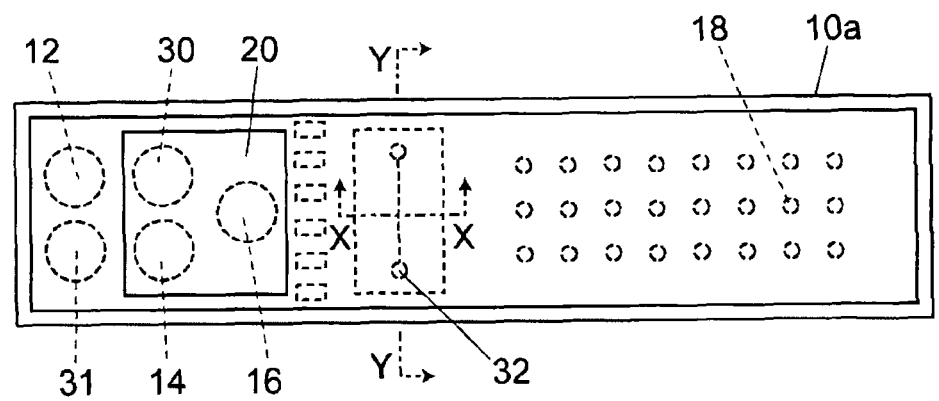
[FIG. 5B] A plan view showing the second example of the reaction vessel.
Figure 5C:
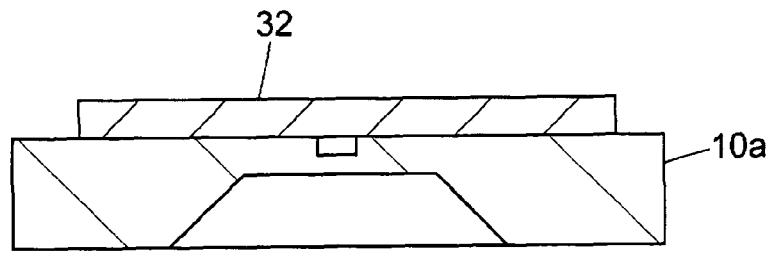
[FIG. 5C] An enlarged section view along the line X-X in FIG. 5B showing the second example of the reaction vessel.
Figure 6A:
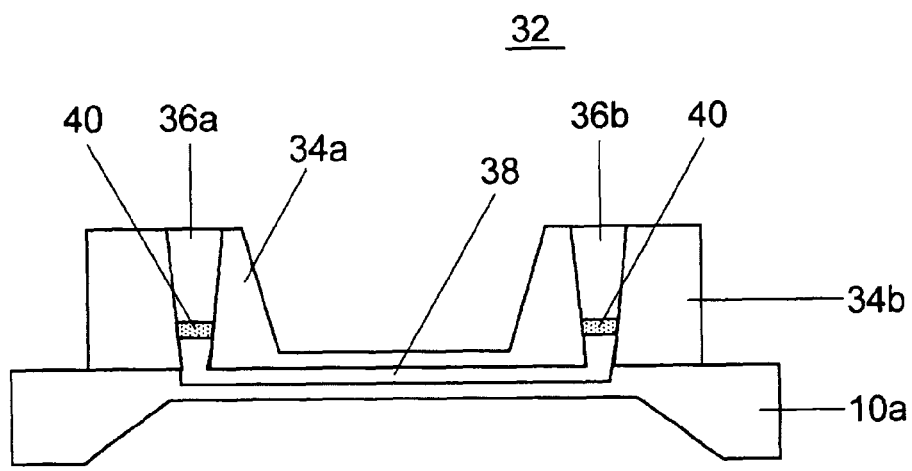
[FIG. 6A] An enlarged section view of an amplification reaction part in the same example along the line Y-Y of FIG. 5B in the condition that a reaction solution is injected.
Figure 6B:
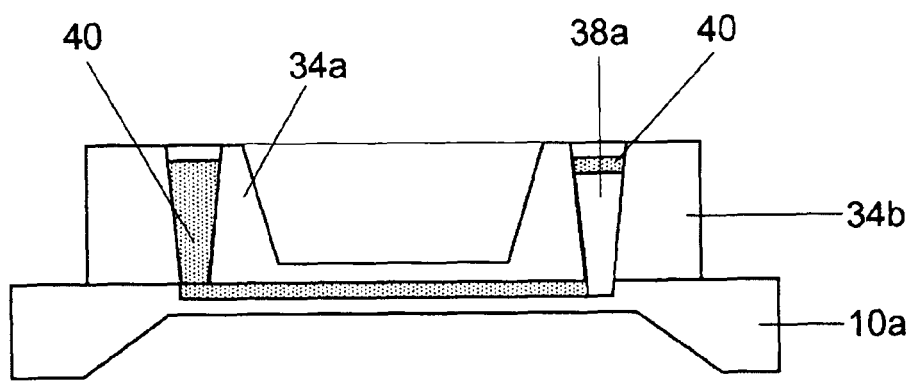
[FIG. 6B] An enlarged section view of the amplification reaction part in the same example along the line Y-Y of FIG. 5B in the condition that the reaction solution is collected.
Figure 7A:
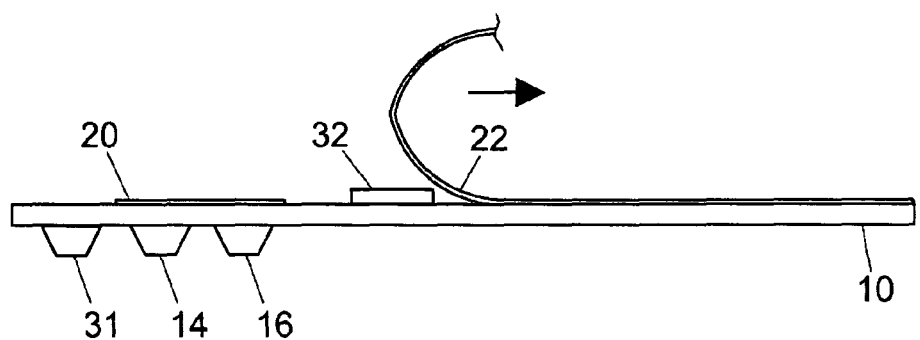
[FIG. 7A] A front view showing a former half of the process of the SNP detection method using the reaction vessel of the same example.
Figure 7B:
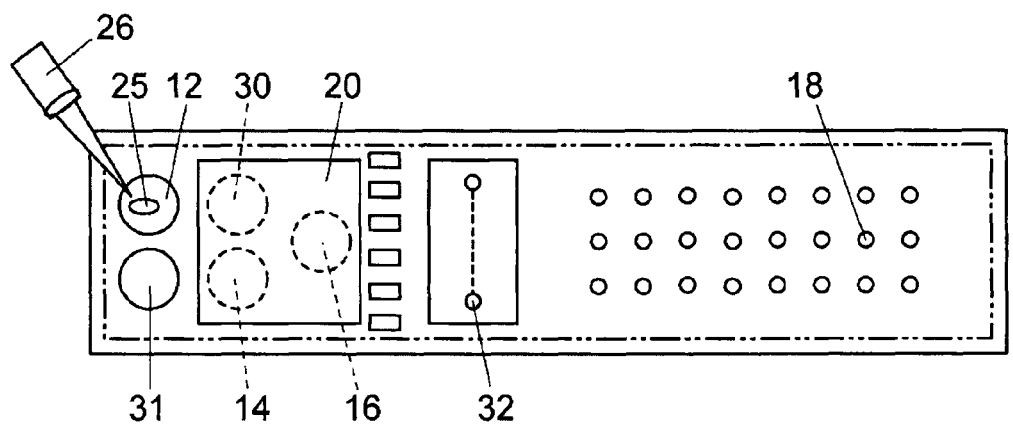
[FIG. 7B] A plan view showing the former half of the process of the SNP detection method using the reaction vessel of the same example.
Figure 8A:
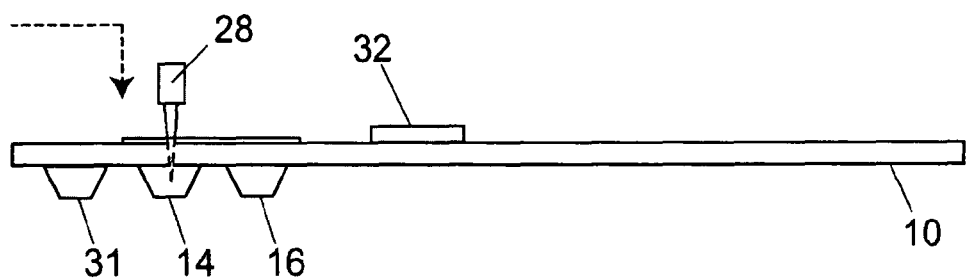
[FIG. 8A] A front view showing a latter half of the process of the SNP detection method using the reaction vessel of the same example.
Figure 8B:
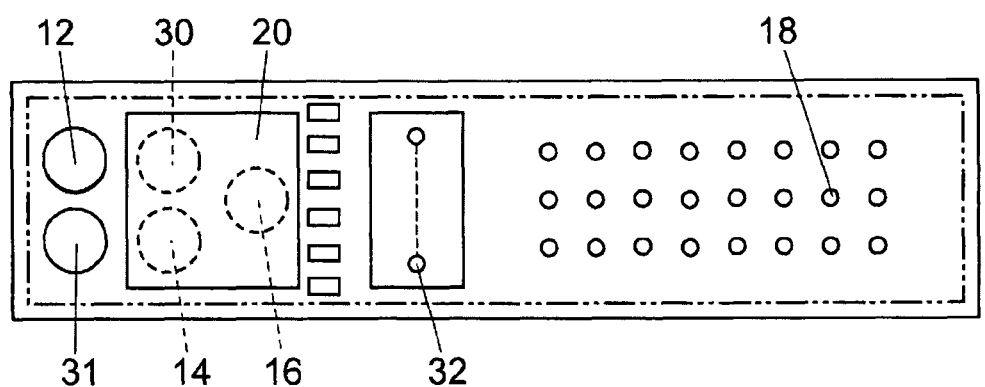
[FIG. 8B] A plan view showing the latter half of the process of the SNP detection method using the reaction vessel of the same example.
Figure 9:
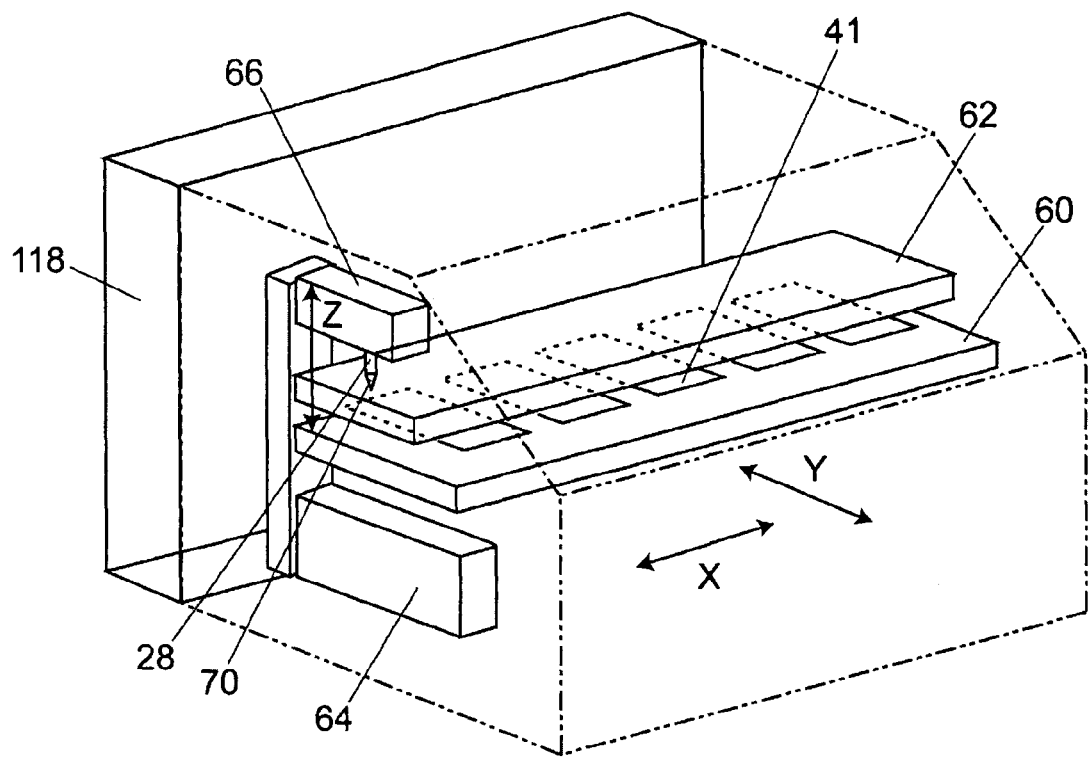
[FIG. 9] A schematic perspective view showing one example of a simplified reaction vessel processing apparatus that uses the reaction vessel of the present invention as a reagent kit, and detects SNP of a biological sample.
Figure 10:
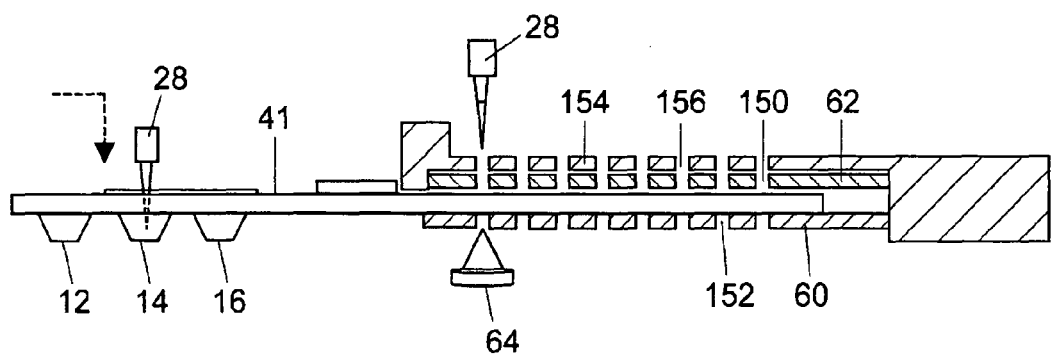
[FIG. 10] A section view showing a typing reaction part in the same example.
Figure 11A:
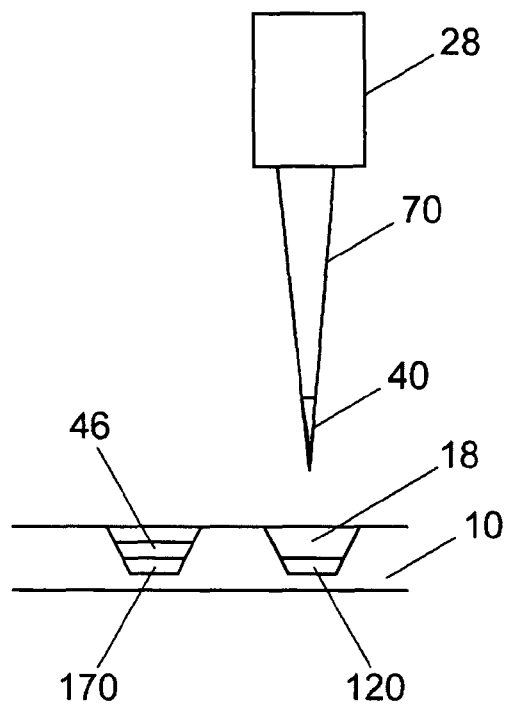
[FIG. 11A] A view showing a method of dispensing mineral oil to a probe arrangement part, which is a general method.
Figure 11B:
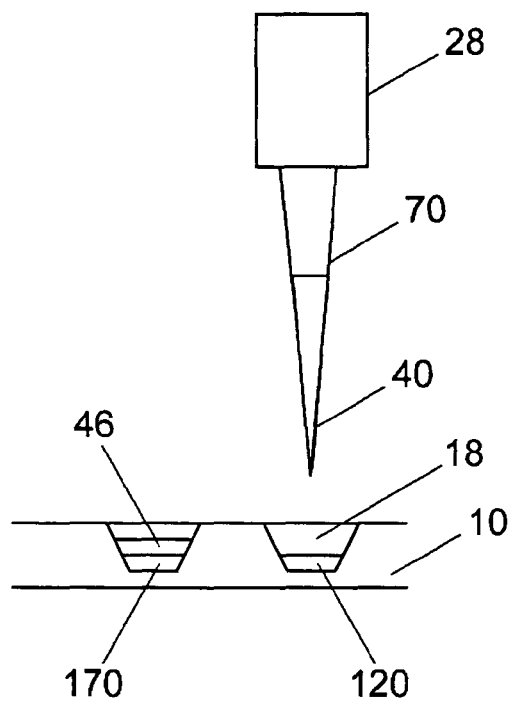
[FIG. 11B] A view showing a method of dispensing mineral oil to a probe arrangement part, which is a method according to the present invention.
Figure 12:
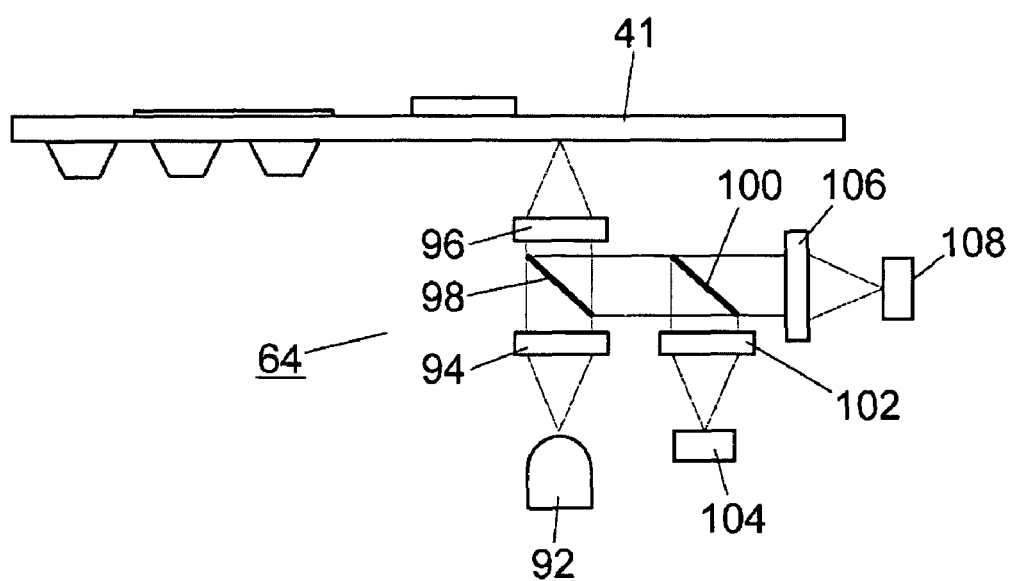
[FIG. 12] A schematic structure view showing a fluorescence detector in the same example.
Figure 13:
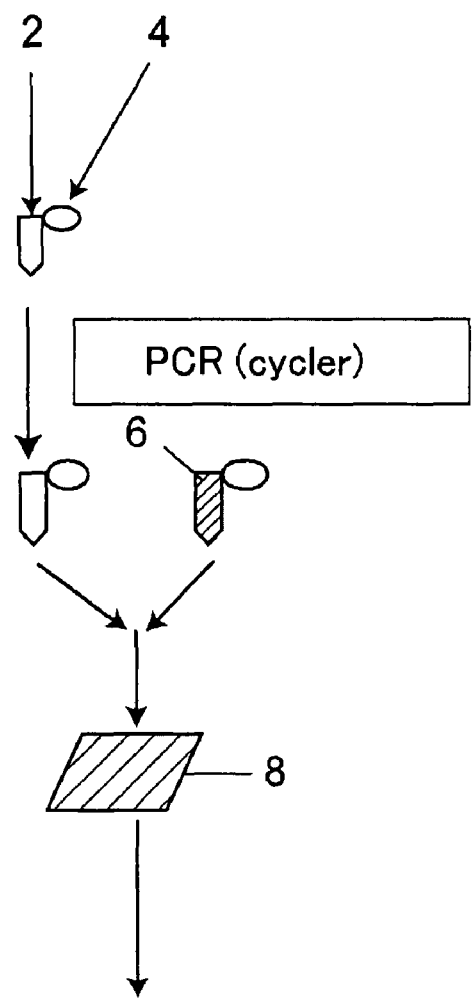
[FIG. 13] A flow chart schematically showing an SNP detection method which may be related to the present invention.
Figure 13:
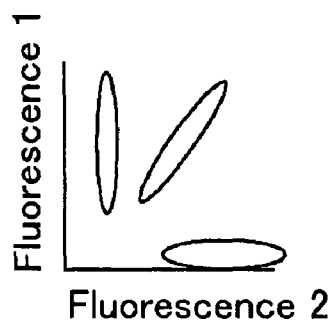

DESCRIPTION OF THE REFERENCE NUMERALS 2 sample
4 PCR reagent
6 invader reagent
8 probe arrangement part
10, 10a substrate
12 sample injection part
14 typing reagent reservoir part
16 mineral oil reservoir part
18 probe arrangement part
20 film
22 sealing material
28 nozzle
30 gene amplification reagent reservoir part
31 PCR-finished solution injection part
32 amplification reaction part
34a, 34b port of amplification reaction part
36a, 36b opening of port
41 reaction vessel
60, 62 heat block
64 detector
66 liquid feeding arm
70 tip
112 Dispenser
118 Controller
150, 152 Opening of heat block.

What is claimed is:

1. A nonvolatile liquid dispensing method comprising:

providing a reaction vessel comprising at least a typing reagent reservoir reserving a typing reagent, a gene amplification reagent reservoir for reserving a gene amplification reagent containing a plurality of primers to bind to a plurality of polymorphic sites by sandwiching each site between the primers, an amplification reaction part that allows a gene amplification reaction for a mixture solution of the gene amplification reagent and a sample, a plurality of probe arrangement parts each individually holding a probe emitting fluorescence in correspondence with each of a plurality of polymorphic sites and a nonvolatile liquid reservoir for reserving the nonvolatile liquid having a lower specific gravity than a reaction solution, the amplification reaction part having two dispensing ports opened upwardly at both ends thereof;

dispensing the nonvolatile liquid into the amplification reaction part before the gene amplification reaction in the condition that an amount more than a single dispensing amount of the nonvolatile liquid is aspirated and held in a nozzle;

dispensing the nonvolatile liquid through one of the dispensing ports of the amplification reaction part after the gene amplification reaction to facilitate collection of a reaction-finished solution, the reaction-finished solution being pushed to the other dispensing port by the dispensing of the nonvolatile liquid; and dispensing the nonvolatile liquid into the probe arrangement parts in the condition that an amount more than a single dispensing amount of the nonvolatile liquid is aspirated and held in the nozzle.

2. The nonvolatile liquid dispensing method according to claim 1, wherein the nonvolatile liquid is a liquid selected from the group consisting of mineral oil, vegetable oil, animal oil, silicone oil and diphenylether.

* * * * *